(12) United States Patent
Shinbori et al.

(10) Patent No.: US 6,618,141 B2
(45) Date of Patent: Sep. 9, 2003

(54) DEVICE FOR MEASUREMENT OF THE SPECTRAL REFLECTANCE AND PROCESS FOR MEASUREMENT OF THE SPECTRAL REFLECTANCE

(75) Inventors: Masashi Shinbori, Oyama (JP); Hiroyuki Kameda, Susono (JP); Kotaro Moroishi, Kawasaki (JP)

(73) Assignee: Ushiodenki Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/011,437

(22) Filed: Dec. 11, 2001

(65) Prior Publication Data

US 2002/0071118 A1 Jun. 13, 2002

(30) Foreign Application Priority Data

Dec. 11, 2000 (JP) .......................... 2000-376053

(51) Int. Cl.⁷ .................................. G01J 3/28
(52) U.S. Cl. ................. 356/326; 356/328; 356/124
(58) Field of Search ................. 356/326, 328, 356/124

(56) References Cited

U.S. PATENT DOCUMENTS 4,423,736 A * 1/1984 DeWitt et al. ............... 600/306
5,754,283 A * 5/1998 Keane et al. .................. 356/73
5,934,278 A * 8/1999 Ishihara et al. ............. 600/476

FOREIGN PATENT DOCUMENTS

JP 55-21088 5/1980

* cited by examiner

*Primary Examiner*—F. L. Evans
*Assistant Examiner*—Kara Geisel
(74) *Attorney, Agent, or Firm*—Nixon Peabody LLP; David S. Safran

(57) ABSTRACT

A device for measurement of the spectral reflectance of a surface where the reflectance factor of light with a certain wavelength can be measured in a wide wavelength range, including the UV range, and in which a reference reflectance factor can be easily obtained. The device for measurement has a light source part with a xenon lamp; a fiber on the incidence side; a measurement head which emits the light transmitted by the fiber via a convergent lens and a diffuser onto the surface of the measuring object and which receives the light reflected by the surface; a fiber on the exit side; and a spectroradiometer which receives the light which has been transmitted by the fiber on the exit side.

10 Claims, 4 Drawing Sheets

DEVICE FOR MEASUREMENT OF THE SPECTRAL REFLECTANCE AND PROCESS FOR MEASUREMENT OF THE SPECTRAL REFLECTANCE

BACKGROUND OF THE INVENTION

1. Field of the Invention

The invention relates to a device for measuring the spectral reflectance of surface reflection light in mirrors, filters, lenses and the like, employed in optical devices. The invention furthermore relates to a process for measuring the spectral reflectance.

2. Description of Related Art

In an optical device, such as an exposure device, a light irradiation device, optical elements are employed such as reflectors, various filters, or lenses. These optical elements often require that the spectral reflectance be measured. The expression "spectral reflectance" is defined as the reflectance factor of light of a certain wavelength. For example, in a mirror fabricated, with a vacuum evaporated film on its surface, to reflect light of only a certain wavelength, as well as a lens or a filter having an anti-reflection film, it is often necessary to measure the spectral reflectance to confirm that the optical properties of the vacuum evaporated film formed or the antireflection film correspond with the computed values for the optical properties.

A conventional device used to measure the reflectance factor of the reflection surface of a mirror, lens, or filter, is shown in Japanese utility model application JP 55-21088. FIG. 6 is a schematic cross section of the arrangement of the JP 55-21088 device for measurement of the reflectance factor. This device for measuring the reflectance factor includes a cage-like body 71, a light source part 72, and a light receiving part 73. The lateral cross section of the cage-like body 71 is pentagonal and the cage-like body 71 has an angled top plate 75 and a bottom plate 77 in which a light transmission opening 76 is formed.

One of the oblique walls of the angled top plate 75 is provided with the light source part 72, while the other oblique wall is provided with the light receiving part 73. The angle of the uppermost part of the angled top plate 75 is defined by the size of the crossing angle at which the optical axis La of the light source part 72 and the optical axis Lb of the light receiving part 73 cross one another on the surface S of the measuring object M. Leg 78, which is one of several legs, projects from the bottom plate 77 and adjoins the surface S.

The crossing angle between the optical axis La of the light source part 72 and the optical axis Lb of the light receiving part 73 is fixed according to the angle of incidence of the light incident on the surface S. For example, in the situation in which the surface S of the reflection surface of a mirror is used to reflect incident light with an angle of incidence of 30 degrees, it is necessary to measure the reflectance factor in the situation in which the light is incident with an angle of incidence of 30 degrees on the surface S. The crossing angle between the optical axis La and the optical axis Lb is therefore 60 degrees in the vicinity of the surface S.

The reflectance factor of a reflection surface is generally the ratio of the change of the reflectance factor to the difference of the angle of incidence which becomes greater as the angle of incidence of the light becomes greater. The above described crossing angle in a device for measuring the reflectance factor is normally fixed in the range from 0 degrees to 120 degrees for the following reasons:

Many practical reflectors are used with an angle of incidence of the light in the range from 30 to 60 degrees.

To determine the characteristic of the antireflection film of a lens or filter, a measurement is taken in the state in which the angle of incidence is 0 degrees.

In the light source part 72 there are a light source lamp 81 and a diffuser 83. The light source lamp 81 is a small halogen lamp. In the light receiving part 73 there are a lens 84 on which the light reflected by the surface S is incident and a light receiving apparatus 85 which consists of a photoelectric cell.

In this device for measuring the reflectance factor, the light from the light source lamp 81 of the light source part 72 is scattered by means of the diffuser 83 and then the light is emitted forward with an irradiance which is uniform in all directions and is emitted via the light transmission opening 76 of the bottom plate 77 of the cage-shaped body 71 onto the surface S. The light reflected by the surface S is incident again via the light transmission opening 76 on the light receiving part 73 and is projected via the lens 84 onto the light receiving surface of the light receiving apparatus 85. Based upon the radiance of the above described reflection light, the reflectance factor of the surface S is determined.

In the light receiving part 73 a state is implemented in which over the entire range of the solid angle, which is viewed from the light receiving surface of the light receiving apparatus 85 via the lens 84, there is the image of the diffuser 83 broadened with a uniform irradiance. The amount of the light received by the light receiving apparatus 85 is therefore independent of the shape of the measuring object, but is proportional only to the reflectance factor of the surface S.

When the reflectance factor is measured by the above described device, it is necessary to obtain a reference which is characteristic of this device for measuring the reflectance factor. Then using this reference, the reflectance factor is determined in the manner described below.

Determination of the reference is done before measuring the reflectance factor of the measuring object or after the measurement task. Specifically, a standard mirror with a known reflectance factor is used to determine the reference. Specifically, light is emitted onto the reflection surface of the standard mirror by means of the device of FIG. 6 which will measure the reflectance factor and the irradiance of the reflection light. In this manner, a reference is determined for device for measuring the reflectance factor of measuring object.

The reflectance factor of the surface S can be obtained by the same computation employed to compute the quotient (a/b) and the spectral reflectance α of the above described standard mirror. That is, for the surface S, the quotient (a/b) is obtained by dividing the value a which is the irradiance of the reflection light obtained with respect to the surface S of the actual measuring object, by the value b which is the irradiance of the reflection light from the standard mirror (reference).

For example, in the case in which the value a of the irradiance of the reflection light measured with respect to the surface S is 7 $mW/cm^2$, and in which the value b of the irradiance of the reflection light is 10 $mW/cm^2$ which was obtained from the standard mirror with a spectral reflectance α of 80%, the reflectance factor of the surface S is computed as follows:

$$(7/10) \times 80(\%) = 56(\%)$$

In the above described device for measuring the reflectance factor the disadvantages are the following:

(1) With respect to the measurement wavelength, when the reflectance factor is measured, it is necessary for the measurement light emitted onto the surface of the measuring object to have the same wavelength as the light which optically treats the above described measuring object for the actual application.

For example, in the situation in which the reflectance factor of an optical element such as a mirror used in a UV exposure device is measured, the desired result cannot be obtained when the reflectance factor of the UV light, with the same wavelength as the UV light which is intended to optically treat the optical element, is not measured. The wavelength of the light for treatment of the optical element can be different depending on the intended use of the optical device. For example, the light can be over a certain UV wavelength range or, alternatively, in a device for exposing a circuit pattern, the light can be a strictly predetermined wavelength of 365 nm which corresponds to the wavelength at which the resist has sensitivity.

It is therefore necessary to confirm that the reflectance factor of light in a certain UV range is high and is low with respect to light in the visible range and infrared range in order to check the optical characteristic of an mirror provided with a vacuum evaporated film used to reflect only the UV light while transmitting the visible radiation and the infrared light. Furthermore, with respect to a lens or a filter which is provided with an antireflection film it is necessary to confirm that the reflectance factor of the light is low over the entire wide wavelength range.

In a conventional device for measuring the reflectance factor, a process is utilized in which the light source lamp 81 is a halogen lamp and a photoelectric cell is used as the light receiving apparatus 85. Therefore, only the reflectance factor for all the light is measured over a wide wavelength range with the center consisting of the visible range, and the spectral reflectance, which is the reflectance factor of light within a certain wavelength, cannot be measured. Since a halogen lamp in the UV range does not have a high emission intensity, the reflectance factor in the UV range cannot be measured.

The above described example, in which the amount of light received by the light receiving apparatus 85 is proportional only to its reflectance factor regardless of the shape of the surface S, means a state exists in which, over the entire range of the solid angle viewed by the light receiving apparatus 85 that receives the reflection light, a reflection surface with uniform irradiance is formed. To form one such reflection surface with a uniform irradiance it is necessary for the diffuser 83 to form a surface light source with a uniform radiance.

FIG. 7 shows a schematic of the action of an ideal diffuser P1. Regardless of the direction of the incident light L1 the transmitted light L2 is uniformly scattered at the respective site on this diffuser P1 in all directions. This diffuser P1 accomplishes a state in which a surface light source with uniform irradiance is formed when viewed from the position in front of the exit side of the light as is shown by arrow V.

Plates of materials, such as opal glass or the like, are known as diffusers having this ideal light scattering function in the visible range and in the infrared wavelength range. They do absorb some light. But since a halogen lamp, in the above described wavelength range, has a high radiation intensity in practice there is no problem.

On the other hand, when a xenon lamp is used as the light source lamp to obtain light in the UV range, and if an attempt is made to take measurements only with respect to certain wavelengths, the radiation intensity becomes low. If a diffuser of a material which absorbs UV light is used, the intensity of the reflection light from the surface is reduced to the "noise level". Therefore, there are situations in which the measurement becomes impossible.

In light of this circumstance, it is necessary to use a diffuser of a material which has high transmission factor with respect to UV light and can also scatter UV light. However, at present, with the exception of quartz frosted glass, there is no diffuser with this property.

Unfortunately, frosted quartz glass does not have sufficient light scattering ability. As shown in FIG. 8, in the situation in which a diffuser P2 of frosted quartz glass is employed the directions of primary scattering differ when the incident light L1 is scattered light. Therefore, a surface light source with an irradiance which has high uniformity in all directions cannot be obtained over the entire surface of the diffuser P2 when viewed from a position in front (direction of the arrow V). As a result the measurement of the reflectance factor cannot be made with high precision.

2) With respect to reduction in size, the above described prior device for measuring the reflectance factor has a structure in which a reduction in size is intended. However, the cross section of its cage-like body 71 has a large pentagonal shape, and the upper region in which the light source part 72 and the light receiving part 73 are located has a great width. If the spectral reflectance of the reflection surface of a small oval focusing mirror, with a small radius of curvature, is measured there are situations in which the top wide area of the cage-like body 71, the wide light source part 72, or the wide light receiving part 73 partially interfere with the measuring object when the radius of curvature of the bent measuring object M is smaller than in the state shown in the drawings using the broken line. There are therefore also cases in which the bottom plate 77 of the above described measurement device which is provided with the light transmission opening 76 is not in the proper position and an exact measurement cannot be made.

3) With respect to obtaining the reference, in the above described device for measurement of the reflectance factor it is necessary to make available a standard mirror with a known reflectance factor in order to obtain a reference. The standard mirror must be carefully stored and handled so that its spectral reflectance does not change over time. However, if the spectral reflectance of the standard mirror changes, the change cannot be determined, thereby resulting in the consequence that errors will arise in the measurement of the spectral reflectance of the measuring object.

SUMMARY OF THE INVENTION

The invention was provided to eliminate the above described defects in the prior art. The object of the invention is to provide a device for measurement of the spectral reflectance in which light in the UV range can be used as measurement light, uniform irradiance can be obtained in a diffuser, and the reflectance factor can be measured in a wide wavelength range, including the UV range, by means of measurement light with a certain wavelength.

Another object of the invention is to provide a device for measurement of the spectral reflectance in which the head part adjoining the measuring object can be reduced in size to a sufficient degree such that even when using an oval focusing mirror with a small radius of curvature, the spectral reflectance of the reflection surface on its inner mirror surface can be measured.

Still another object of the invention is to provide a device for measurement of the spectral reflectance in which the reference can be easily obtained without using a standard mirror with a known spectral reflectance.

Still another object of the invention is to provide a process for measurement of the spectral reflectance by means of the above described device for measurement of the spectral reflectance.

These objects are achieved in a device for measurement of the spectral reflectance by providing the following features:

a light source part with a xenon lamp;

an optical fiber on the incidence side which transmits light from the above described light source part;

a measurement head which emits the light, transmitted by the optical fiber on the incidence side via a convergent lens and a diffuser, onto the surface of the measuring object and receives the light reflected by the above described surface;

an optical fiber on the exit side which transmits the reflection light which has traveled through the measurement head; and a spectroradiometer which receives the light which has been transmitted by the optical fiber on the exit side.

Within the framework of the invention the expressions "optical fiber" or "fiber" designates both a single fiber and a bunch of fibers consisting of several fibers.

The objects of the invention are further achieved in the above described device for measurement of the spectral reflectance in an embodiment in which measurement head has a light incidence holder and a light emergence holder which is independent and separate of the light incidence holder. The light incidence holder has on one end a fiber connection part to which the fiber on the incidence side is connected; while, on the other end of the light incidence holder a light transmission opening is provided. Proceeding from the side of the fiber connection part, the convergent lens and the diffuser are located in sequence in the light incidence holder. In the light emergence holder, there is a lens for receiving the light reflected by the surface situated between one end which is located opposite the surface S, and the other end which is provided with the fiber connection part to which the fiber is connected on the exit side. Furthermore, the light incidence holder and the light emergence holder are coupled in one piece in the manner to be separable from one another so that the respective optical axes on the surface S of the measuring object M or in the vicinity thereof cross each other.

The objects of the invention are furthermore achieved in an embodiment in which in the light emergence holder of the measurement head there is a mirror which reflects the light reflected from the surface such that the direction in which the light emergence holder extends is essentially identical to the direction in which the light incidence holder extends, such that their axes are substantially parallel.

The objects of the invention are furthermore achieved in an embodiment in which the light incidence holder and the light emergence holder of the measurement head can be coupled to one another in such a manner that the optical axes of the two holders agree with one another, and such when in such a coupled state, with respect to the reference light, a reference light measurement can be taken. In this embodiment, an arrangement can be provided in which the light incidence holder and the light emergence holder can be coupled to one another by means of a template for reference light measurement.

The objects of the invention are furthermore achieved by a process for the measurement of the spectral reflectance using the above described device for measurement of the spectral reflectance where the light incidence holder and the light emergence holder are coupled to one another in a manner in which the optical axes of the two are in agreement, i.e., substantially parallel, with each other so that the reference light is measured, and where the light incidence holder and the light emergence holder of the measurement head are coupled to one another in a manner in which the respective optical axes cross on the surface of the measuring object or in the vicinity such that the spectral reflectance of the measuring object surface is measured. Therefore, based upon the relation between the spectral irradiance of the reference light and the spectral irradiance of the reflection light, the spectral reflectance of the surface is determined.

The objects of the invention are furthermore achieved by a device for measurement of the spectral reflectance by the following features:

a light source part with a xenon lamp;

an optical fiber on the incidence side which transmits light from the above described light source part;

a measurement head which emits the light, transmitted by the fiber on the incidence side via a convergent lens, a diffuser, and a semi-transparent mirror, onto the surface of the measuring object and moreover which receives the light reflected by the above described surface via the semi-transparent mirror; and an optical fiber on the exit side which transmits the reflection light which has traveled through the measurement head; and a spectroradiometer which receives the light which has been transmitted by the above described fibers on the exit side.

The device for measurement of the spectral reflectance of the above described arrangement can employ a xenon lamp as the light source lamp, and, moreover, a spectroradiometer for determining the illuminance of the reflection light. Therefore, the spectral reflectance can be measured at the respective wavelength in a wide range of wavelengths from the UV range, upto the visible and the infrared range.

Furthermore, the light source part and the measurement head are optically connected to one another via the optical fibers. The measurement head and the spectroradiometer are similarly optically connected to one another via the optical fibers. The degree of versatility with respect to the given arrangement of the light source part, the measurement head, and the spectroradiometer is therefore great.

Additionally, the measurement head on the invention can be made to have a smaller configuration since when measuring the spectral reflectance it is satisfactory to move only the tip area of the small measurement head close to the surface, such that measurement of the spectral reflectance for a focusing mirror with a small radius of curvature and in a narrow range is possible.

It is noted that the reference can be easily obtained directly by means of the above described device for measurement of the spectral reflectance when the measurement head is reassembled into the state for reference light measurement. As a result, a standard mirror with a known reflectance factor is not needed. Furthermore, in the conventional situation for reference measurement using a standard mirror the change of the reflectance factor of the standard mirror can also be measured.

DETAILED DESCRIPTION OF THE INVENTION

Figure 1:
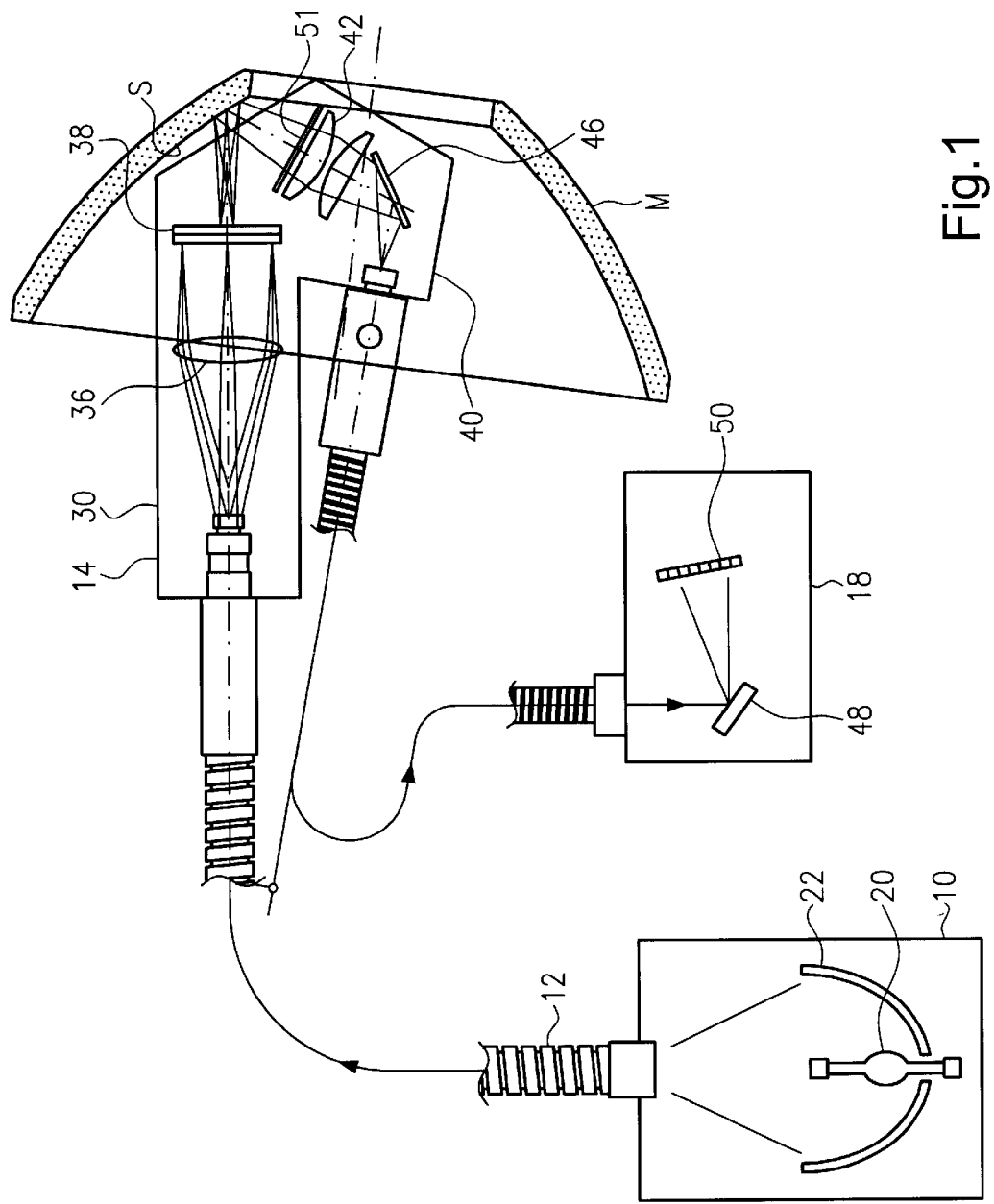
FIG. 1 shows a schematic of one example of the device of the invention for measurement of the spectral reflectance.

FIG. 1 is a schematic of one embodiment of the device for measuring the spectral reflectance where the measuring object M, shown in cross section, is a concave mirror. The device for measuring the spectral reflectance in this example has a light source part 10, a measurement head 14 that is connected to one end of a fiber 12 on the incidence side, with the other end of the fiber 12 being connected to the light source part 10, and a spectroradiometer 18 which is connected to an end of fiber 16 of suitable length emerging on the exit side from the measurement head 14.

The light source part 10 consists of a xenon lamp 20 as the light source and an oval focusing mirror 22 which focuses the light which has emerged from this xenon lamp 20. The one end of the fiber on the incidence side 12 is located at the focal position of the light from the oval focusing mirror 22. Here the xenon lamp 20 is a discharge lamp which emits continuous light in a wavelength range of greater than or equal to 200 nm to 800 nm.

Figure 2:
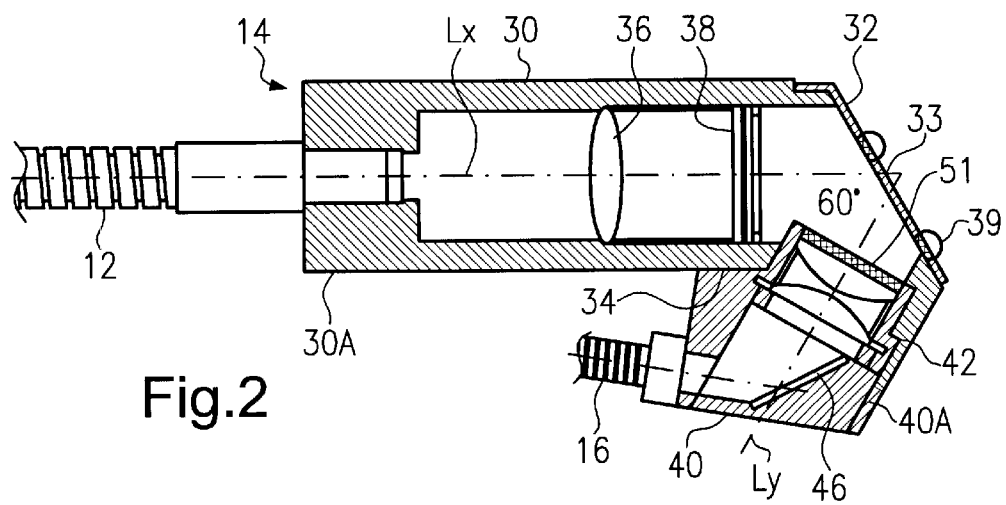
FIG. 2 shows a schematic cross section of a specific arrangement of a measurement head of the invention.

FIG. 2 is a cross section of the specific arrangement of a measurement head 14. The measurement light transmitted by the fibers 12 on the incidence side (light before reaching the surface S) is incident on this measurement head 14. The measurement head 14 includes of a light incidence holder 30 from which the measurement light emerges in the direction to the surface S and a light emergence holder 40 on which the reflection light from the surface S (the light reflected by the surface S) is incident and which in turn allows light to be incident on the fiber 16 on the exit side.

The light incidence holder 30 on one end has a connection part 30A to which the exit end of the fiber 12 is connected. On the other end of the light incidence holder 30, along a surface which obliquely crosses the optical axis Lx of the light incidence holder 30, is a front plate 32 with a light transmission opening 33 formed in the center and through which the measurement light and the reflection light pass. In the middle area of this light incidence holder 30, there is a collimator which includes a convergent lens 36 and then a diffuser 38 composed of frosted quartz glass. Here the convergent lens 36 is designed to convert the incident light into parallel light; while the diffuser 38 makes the irradiance uniform. Projection legs 39 project away from the front plate 32. In operation, the measurement head 14 is placed on the surface S via these projection legs 39.

Additionally, there is the light emergence holder 40 which is separable and independent of the light incidence holder 30. On one end light emergence holder 40 has a lens 42 which receives and adjusts the reflection light from the surface S and on the other end a connection part 40A on the exit side to which the end of the fiber 16 is connected. Furthermore, there is a mirror 46 which deflects the optical path of the reflection light from the lens 42 in a direction which has essentially the same direction as the light incidence holder 30, that is, the direction of the reflection light gradually slopes toward the holder 30, The reflector thus enables the reflection light to be incident on the incidence end of the fiber 16. In this arrangement, the direction in which the light emergence holder 40 extends crosses, at a small angle of for example 10 degrees, the direction in which the light incidence holder 30 extends.

The outside peripheral surface of the end of the light incidence holder 30 and the outside peripheral surface of the end of the light emergence holder 40 are provided with an engagement surface part 34 which causes, when in the arrangement shown, the two peripheral surfaces to engage one another. In this engaged state, i.e., in the state in which the light incidence holder 30 and the light emergence holder 40 are in a certain positional relationship, the holders are separably coupled as a single unit. In one such attached state, the optical axis Lx of the light incidence holder 30 and the optical axis Ly of the light emergence holder 40 cross each other with a given angle, e.g., 60 degrees, on the surface S or at a point in the vicinity of surface S, as shown in FIG. 2. This arrangement of the measurement head 14 is the state for an accurate measurement. The angle of incidence of the measurement light with respect to the surface S is 30 degrees in this example.

To attach the light incidence holder 30 and the light emergence holder 40 to one another, a suitable attachments means can be used. For example, in conjunction with the engagement surface part 34 an insertion device can be constructed which mechanically inserts the two holders into one another. Furthermore, an attachment component such as a coupling component, a vise or the like can be used to attach the holders.

In the spectroradiometer 18 there is an optical sensor 50 which receives the reflection light transmitted by the fiber 16 via a spectral element 48 which consists of a prism or a grating or similar device.

The above described measurement head 14 has an arrangement in which it is possible to change from the structure shown in FIG. 2 into a structure for reference light measurement to acquire the reference value. This is done separating and changing the light incidence holder 30 and the light emergence holder 40 from one positional relationship to another.

Figure 3:
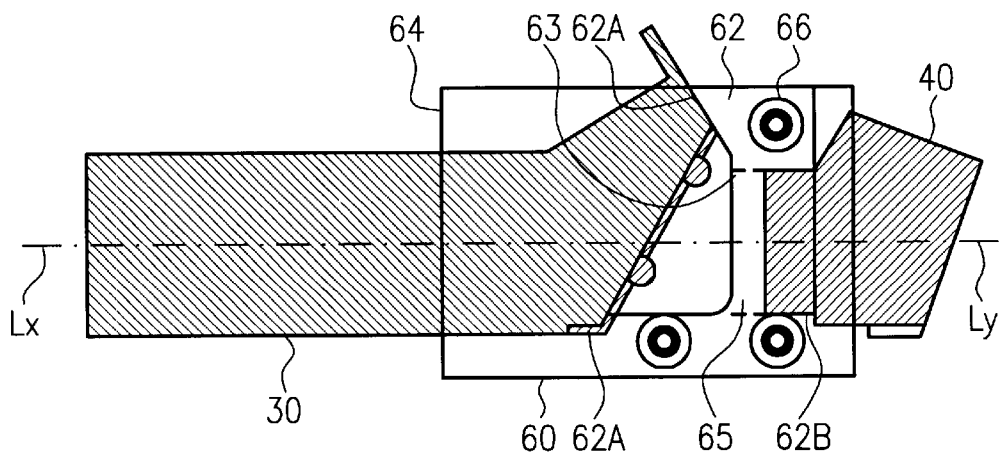
FIG. 3 shows a schematic side view which illustrates the measurement head when configured for reference light measurement.
Figure 4:
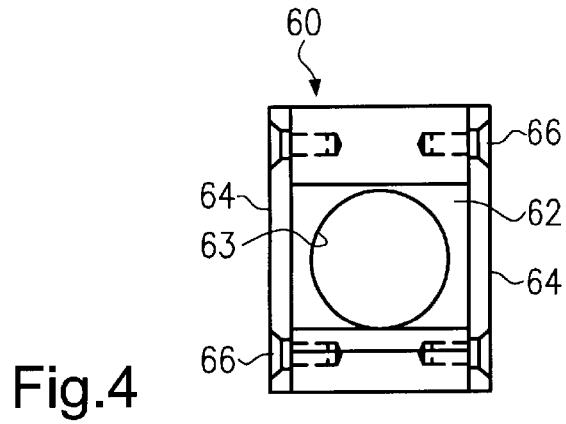
FIG. 4 shows a front view of the embodiment where a template for reference light measurement according to FIG. 3 is used.

FIG. 3 is a schematic side view of a structure in which the light incidence holder 30 and the light emergence holder 40 of the measurement head 14 are coupled to one another by means of a template 60 for reference light measurement. FIG. 4 is a front view of the structure in which the template 60 for reference light measurement as shown in FIG. 3 is viewed from the left.

In FIG. 3 the light incidence holder 30 and the light emergence holder 40 are of a structure which proceeds from the state shown in FIG. 2, such that the holders have been turned entirely around the optical axis Lx by 180 degrees and in which the light emergence holder 40 has been turned to the right by 60 degrees around the axis which is perpendicular to the page of the drawings.

In the measurement head 14, the structure for a true measurement is desired, the light incidence holder 30 and the light emergence holder 40 are separated from one another by releasing the engagement of the engagement surface part 34. Furthermore, the light emergence holder 40 is turned and one of its ends is directly opposite the other end of the light incidence holder 30. Furthermore, the light incidence holder 30 and the light emergence holder 40 are arranged so that the optical axis Ly of the light emergence holder 40 coincides or aligns with the extension of the optical axis Lx of the light incidence holder 30. In addition, the two holders are assembled with a gap 65 of suitable length by means of the template 60 which functions to attach the two holders. In this construction, the two holders are assembled such that the length of the optical path between the diffuser 38 of the light incidence holder 30 and the lens 42 of the light emergence holder 40 is identical to length required for the true measurement.

Specifically, in the template 60 a first engagement part 62A, which is joined to the outer side of the other end of the light incidence holder 30, and a second engagement part 62B, which is joined to the outer side of the other end of the light emergence holder 40, are provided. Furthermore, the template 60 has a part 62 for controlling the central position in which light transmission through opening 63 occurs, and has a pair of clamping plates 64 located opposite each other and bordering the two sides of the part 62 such that the part 62 and plates 64 are coupled to one another by means of a vise elements 66.

In the construction in which the other end of the light incidence holder 30 and one end of the light emergence holder 40 are inserted adjacently into the first engagement part 62A and into the second engagement part 62B of the part 62, respectively, for controlling the middle position, the light incidence holder 30 and the light emergence holder 40 are in a positional relationship for reference light measurement.

The spectral reflectance is determined in the manner described below with respect to the surface S of the measuring object M by the device for measuring the spectral reflectance of the above described arrangement.

When the measurement head 14 is in the state shown in FIG. 2 for a true measurement and when the xenon lamp 20 of the light source part 10 is operated, the light from this xenon lamp 20 is focused by the oval focusing mirror 22 and is incident on one end of the fiber 12 with an angle of incidence which is fixed by the numerical aperture (NA) of the fiber 12 on the incidence side. This light is transmitted through the fiber 12 on the incidence side as the angle of incidence is kept constant and is incident on its other end on the light incidence holder 30 of the measurement head 14 as measurement light.

In the light incidence holder 30 the measurement light from the fiber 12 is incident on the collimator lens 36 in the state in which it propagates with an angle which corresponds to the above described angle of incidence, is converted into parallel light by the collimator lens 36, and emerges. The measurement light which has been converted into this parallel light passes through the diffuser 38.

Figure 5:
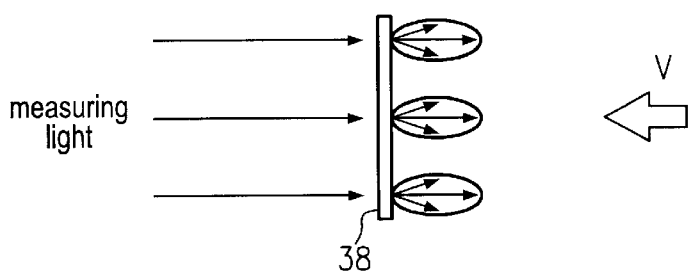
FIG. 5 shows a schematic of the action of the diffuser in one embodiment of the invention.
Figure 6:
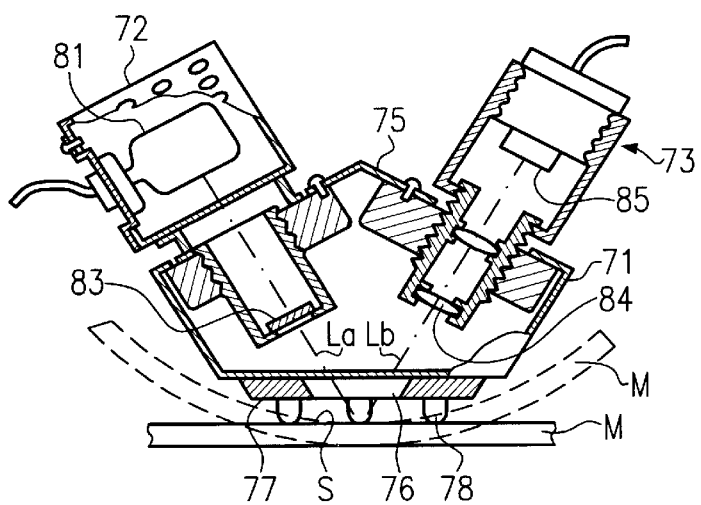
FIG. 6 shows a schematic cross section of a conventional device for measurement of the reflectance factor.
Figure 7:
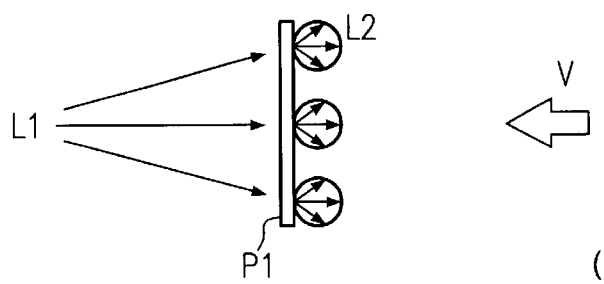
FIG. 7 shows a schematic of the action of an ideal diffuser.
Figure 8:
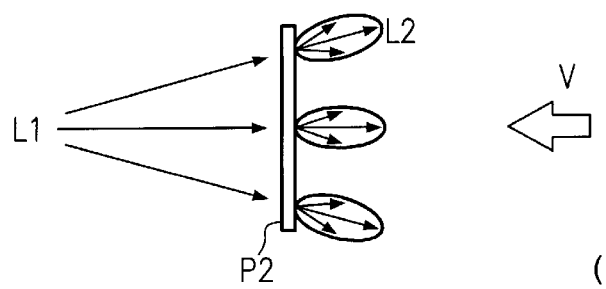
FIG. 8 shows a schematic of the action of the diffuser in the device for measurement of the reflectance factor according to FIG. 6.

The diffuser 38 consists of frosted quartz glass, as described above which does not have a sufficient light scattering property. However, since the directivity of the incident light is uniform, the measurement light from this diffuser 38 has high uniformity of radiance at all points on the overall surface of the diffuser 38 when looking from the direction of the front shown using the arrow V (i.e., front on the exit side of the light), as is shown in FIG. 5. This measurement light with radiance which has been rendered uniform is emitted by the light transmission opening 33 of the front plate 32 in the direction to the surface S of measuring object M.

This emitted measurement light is reflected by the surface S. This reflection light is incident in the state in which the irradiance is uniform in the light emergence holder 40 and from there via the lens 42 and the mirror 46 on the fiber 16 on the exit side.

The angle of incidence of the refection light incident on the fiber 16 on the exit side is fixed by the numerical aperture (NA) of the fiber 16 on the exit side. When the angle, when viewing the area with the uniform radiation intensity on the surface S from the incidence end of the reflection light of the fiber 16 on the exit side, is greater than the above described numerical aperture, the reflection light with a uniform irradiance is incident on the fiber 16 on the exit side.

The reflection light transmitted by the fiber 16 on the exit side is incident in the spectroradiometer 18 which is connected to the other end of the fiber 16, and in the spectroradiometer 18 the reflection light is subjected to spectral diffraction by means of the spectral element 48. The amount of light with the respective wavelength is determined by the optical sensor 50. In this way the spectral irradiance is measured.

The spectral irradiance with respect to the surface S is measured in the above described sequence. To determine its spectral reflectance from this, the reference must however be obtained which takes place in the following sequence.

The light incidence holder 30 and the light emergence holder 40 of the measurement head 14 are coupled to one another using the template 60 for reference light measurement and attached such that they are in the state for reference light measurement shown in FIG. 3.

When in this state for reference light measurement, the light from the light source part 10 is incident via the fiber 12 on the incidence side on the light incidence holder 30, the light is converted into parallel light by the collimator 36 in the same manner as described above, the irradiance is rendered uniform by the diffuser 38 and then emerges from the light transmission opening 33 of the front plate 32. This emerged light passes through the light transmission through opening 63 of the part 62 for controlling the middle position and through the gap 65 and is incident on the light emergence holder 40.

The light which was incident on this light emergence holder 40, as in the case of the state for the true measurement, is incident via the lens 42 and the mirror 46 on the fiber 16 on the exit side and is delivered to the spectroradiometer 18 by which the spectral irradiance of the light is measured; this is stored as the reference. The reference obtained in this way is identical to the value obtained for a standard mirror with a reflectance factor of 100%.

The measured value for the actual measuring object in the already described state for true measurement with respect to light with a given wavelength is divided by the reference with respect to light with this wavelength, by which a quotient is obtained. In this way the spectral reflectance is determined with respect to this measuring object.

The above described device for measuring spectral reflectance yields the following effects:

(1) The reflectance factor of the light at the given wavelength, i.e., the spectral reflectance, can be measured in a wide wavelength range from the UV range to the visible range and to the infrared range. The reason for this is that in the light source part 10 the xenon lamp 20 which emits in a continuously wide wavelength range from the UV range to the infrared range including the visible range is used as the light source lamp, and that the irradiance of the light at the respective wavelength is measured by the spectroradiometer 18 which can measure irradiances with a certain wavelength.

(2) Since the light source part 10 is optically connected to the measurement head 14 and the measurement head 14 to the spectroradiometer 18 respectively via the fiber 12 on the incidence side and the fiber 16 on the exit side, the light source part 10, the measurement head 14 and the spectroradiometer 18 can be freely arranged without major mutual limitation. Since the measurement head 14 is essentially independent of the light source part 10 and the spectroradiometer 18, it can be made smaller. It is therefore possible to measure the reflectance factor for a focusing mirror with a small radius of curvature and in a narrow range.

(3) Since in the light incidence holder 30 the measurement light is converted by means of the collimator 36 into parallel light and this parallel light is furthermore scattered by means of the diffuser 38 of frosted quartz glass, the light emerging from the diffuser 38 has an irradiance which has high uniformity in a certain direction. Therefore the surface S can be irradiated with light with uniform irradiance without reducing the amount of light even when the light is UV light. As a result, for an optical element for treatment with UV light its spectral reflectance can be measured with high reliability.

(4) The light incidence holder 30 and the light emergence holder 40 are separably joined to one another by the arrangement in the example shown in the drawings by their being located adjacently along the engagement surface part 34 which is located on their outside peripheral surfaces. They are coupled to one another in this state and are shifted into the state for true measurement. This enables the front area of the measurement head 14 to be reduced in size; while at the same time this front area is formed at an angle. In the light emergence holder 40 the optical path of the reflection light is deflected by the mirror 46 and runs essentially in the same direction as the light incidence holder 30. In this way there is a configuration in which there is no area which projects forward from the measurement head 14. Therefore, for example, for a reflection surface on the inside of an oval focusing mirror with a small radius of curvature the measurement head 14 can be shifted reliably and easily into the correct state with respect to the measuring object. Therefore the spectral reflectance can be exactly measured.

Since the directions of the light incidence holder 30 and of the light emergence holder 40 are uniform, the direction in which the fiber 12 runs on the incidence side is essentially uniform and identical to the direction in which the fiber runs on the exit side. In this way the two fibers can be combined and thus the region of the measurement head 14 can be reduced in size. At the same time very easy operation is enabled.

(5) Because the measurement head 14 using the template 60 for reference light measurement can be assembled into the configuration for reference light measurement, the reference can be easily obtained by this device for measuring the spectral reflectance. It is therefore unnecessary to make available a standard mirror with a known reflectance factor. Therefore elaborate storage and care of the standard mirror can be abandoned.

However, even a standard mirror is to be used for obtaining the reference the change of the spectral reflectance of the standard mirror can be determined, eliminating the danger that a error will arise in the measured value of the spectral reflectance.

The invention was specifically described above using one embodiment. But the invention is susceptible to numerous modifications. For example, for the light incidence holder light which has been made essentially parallel can be allowed to be incident on the diffuser 38 which is obtained using another convergent lens instead of a collimator which converts the measurement light into parallel light. However, in this case, the uniformity of the radiance of the light on the diffuser 38 is slightly reduced. The measurement accuracy is reduced according to this amount. A diffuser of a material other than frosted quartz glass can also be used when the intensity of the reflection light is relatively great for a determination.

To measure the reflectance factor in a relatively narrow region of the surface S, there are cases in which the region to be irradiated with the measurement light is made narrower. In this situation, however, there are cases in which the angle is smaller, when viewing the area with the uniform irradiance on the surface S from the incidence end of the reflection light of the fiber on the exit side, than the numerical aperture of the fibers 16 on the exit side. When this happens a shutter 51 in placed on the incidence side of the lens 42. This is done so that only the reflection light with a uniform distribution of irradiance is incident on the fibers 16 on the exit side.

Figure 9:
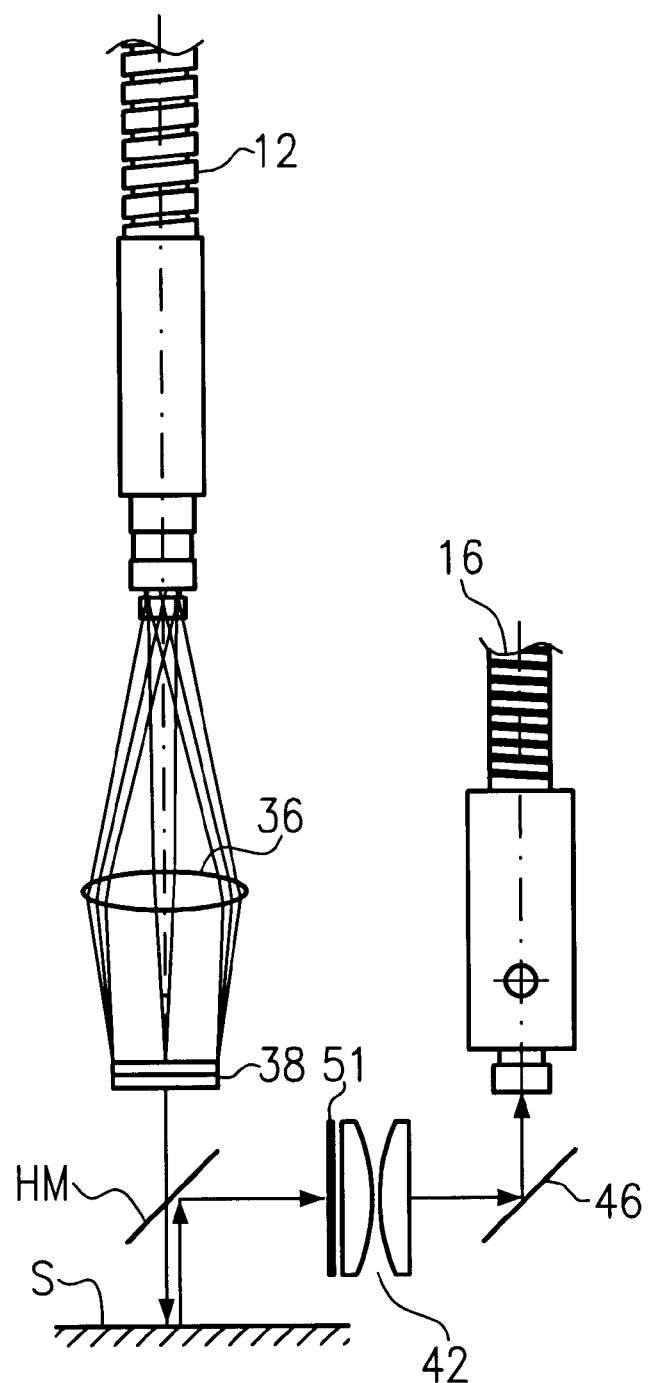
FIG. 9 shows a schematic of the arrangement of the measurement head for measuring the reflectance factor when the angle of incidence is 0 degrees.

FIG. 9 is a schematic of the measurement head in a device of the invention for measuring the spectral reflectance when measurement of the reflectance factor occurs for an angle of incidence of 0 degrees. One such example of this situation occurs when it is necessary to measure the reflection characteristic of an antireflection film which is located in a lens or a filter.

In this arrangement, the light from the fiber 12 on the incidence side is converted into parallel light by means of the collimator 36 and is incident in the diffuser 38. The surface S is irradiated via a semitransparent mirror HM with measurement light with uniform irradiance. The light reflected by the surface S is reflected by the semitransparent mirror HM, and after passing through the lens 42 is deflected by the mirror 46 and is incident on the fiber 16 on the exit side.

The spectral reflectance of a surface S can be measured with this arrangement when the angle of incidence is 0 degrees.

It is advantageous that the fibers on the incidence side and the fibers on the exit side are detachably connected to an inlet end of the light incidence holder and to the exit end of the light emergence holder, respectively. This simplifies movement or transport of the above described device for measuring the spectral reflectance. Further, the installation of the device for measuring the spectral reflectance is simplified.

The means for achieving the constructions for reference light measurement can have various arrangements. It is certainly desirable to use an independent template for reference light measurement. However, for example, if a suitable insertion means is formed in the light incidence holder and the light emergence holder, a template for reference light measurement is not absolutely essential.

Action of the Invention

The device for measurement of the spectral reflectance with the above described arrangement uses a xenon lamp as the light source lamp and moreover a spectroradiometer for determining the illuminance of the reflection light. Therefore the spectral reflectance can be measured at the respective wavelength in a wide range of wavelengths from the UV range to the visible range and to the infrared range.

Since the light source part is optically, detachably connected to the measurement head and the measurement head is optically, detachably connected to the spectroradiometer via the optical fibers, the degree of freedom with respect to the given arrangement of the light source part, the measurement head and the spectroradiometer is great. The measurement head can be made smaller, such that when measuring the spectral reflectance it is enough to move only the tip area of this small measurement head close to the surface, and therefore, measurement of the spectral reflectance for a focusing mirror with a small radius of curvature and in a narrow range is enabled.

Furthermore, the reference can be easily obtained directly by means of the above described device for measurement of the spectral reflectance by employing components of the measurement head that can shifted into the configuration necessary for reference light measurement. Therefore a standard mirror with a known reflectance factor need not be made available.

What is claimed is:

1. A device for measuring the spectral reflectance of the surface of a measuring object and having a light incidence side and a light exit side comprising:

a light source part comprising a xenon lamp on the incidence side;

a measurement head which emits light transmitted from the light source part via a convergent lens and a diffuser onto the surface of the measuring object and which receives the light reflected by the surface of the measuring object;

a fiber on the incidence side which transmits light from the light source part to the measurement head;

a fiber on the exit side which transmits reflected light from the surface of the measuring object which has traveled through the measurement head; and a spectroradiometer on the exit side which receives the reflected light which has been transmitted by the fiber on the exit side.

2. A device for measuring spectral reflectance as set forth in claim 1, wherein the measurement head comprises a light incidence holder and a light emergence holder in which each holder has an optical axis and is separably assembled to the other, wherein the incidence holder includes on one end a fiber connection part for connection of the fiber on the incidence side and includes on another end a light transmission opening and further includes in a direction of incident light a convergent lens and then a diffuser, wherein the light emergence holder includes on one end located opposite the surface of the measuring object and adjacent the light transmission opening a lens which receives light reflected by the surface of the measuring object, and includes on another end on the exit side a connection part for the fiber on the exit side, and wherein each holder can be assembled with the other holder such that the optical axes cross or are aligned.

3. A device for measuring spectral reflectance as set forth in claim 2, wherein the light emergence holder includes a mirror positioned to reflect light reflected by the surface of the measuring object in a direction extending essentially along a longitudinal direction of the light incidence holder.

4. A device for measuring spectral reflectance as set forth in claim 2, wherein the light incidence holder and the light emergence holder of the measurement head are assembled to one another in a configuration in which the optical axes align such that reference light measurements can be made.

5. A device for measuring spectral reflectance as set forth in claim 3, wherein the light incidence holder and the light emergence holder of the measurement head are assembled to one another in a configuration in which the optical axes cross with one another such that spectral reflectance measurements of the surface of a measuring object can be performed.

6. A device for measuring spectral reflectance as set forth in claim 4, wherein the light incidence holder and the light emergence holder are assembled to one another for reference light measurement by means of a template.

7. A device for measuring spectral reflectance as set forth in claim 1, wherein the measurement head comprises a light incidence holder and a light emergence holder each of which have an optical axis and are separably assembled to each other by a template in a configuration in which the optical axes align such that reference light measurements can be made.

8. A process for measuring spectral reflectance of the surface of a measuring object comprising the steps of:

providing the device for measuring spectral reflectance of claim 2, assembling the light incidence holder and the light emergence holder of the measurement head to each another by means of a template in a configuration in which the optical axes align, performing reference irradiance light measurements, reassembling the light incidence holder and the light emergence holder of the measurement head along an engagement surface of each holder in a configuration in which the optical axes cross, and performing irradiance reflected light measurement of the surface of the measuring object, wherein based on the relation between the irradiance of the reference light and the irradiance of the reflected light the spectral reflectance of the surface of the measuring object is determined.

9. A process for measuring spectral reflectance of the surface of a measuring object comprising the steps of:

providing the device for measuring spectral reflectance of claim 2, assembling the light incidence holder and the light emergence holder of the measurement head to each another in a configuration in which the optical axes align, performing reference irradiance light measurements, reassembling the light incidence holder and the light emergence holder of the measurement head in a configuration in which the optical axes cross at the surface of the measuring object, and performing irradiance reflected light measurement of the surface of the measuring object, wherein based on the relation between the irradiance of the reference light and the irradiance of the reflected light the spectral reflectance of the surface of the measuring object is determined.

10. A device for measuring the spectral reflectance of the surface of a measuring object and having a light incidence side and a light exit side comprising:

a light source part comprising a xenon lamp on the incidence side;

a measurement head which emits the light transmitted from the light source part via a convergent lens, a diffuser and a semi-transparent mirror onto the surface of the measuring object and the light reflected by the surface of the measuring object via the semi-transparent mirror;

a fiber on the incidence side which transmits light from the light source part to the measurement head;

a fiber on the exit side which transmits reflected light from the surface of the measuring object which has traveled through the measurement head; and a spectroradiometer on the exit side which receives the reflected light which has been transmitted by the fiber on the exit side.

* * * * *